US008496620B2

(12) United States Patent
Constantz et al.

(10) Patent No.: US 8,496,620 B2
(45) Date of Patent: Jul. 30, 2013

(54) FLUID DELIVERY SYSTEMS FOR DELIVERING FLUIDS TO MULTI-LUMEN CATHETERS

(75) Inventors: Brent R. Constantz, Menlo Park, CA (US); Peter K. Johansson, Campbell, CA (US)

(73) Assignee: Cordis Corporation, Miami Lakes, FL (US)

( * ) Notice: Subject to any disclaimer, the term of this patent is extended or adjusted under 35 U.S.C. 154(b) by 728 days.

(21) Appl. No.: 11/267,944

(22) Filed: Nov. 4, 2005

(65) Prior Publication Data

US 2006/0178621 A1 Aug. 10, 2006

Related U.S. Application Data

(63) Continuation of application No. 09/648,282, filed on Aug. 24, 2000, now abandoned.

(51) Int. Cl.
*A61M 29/00* (2006.01)
*A61M 1/00* (2006.01)

(52) U.S. Cl.
USPC .......................... 604/151; 604/96.01

(58) Field of Classification Search
USPC ............. 604/101.01, 101.03, 101.05, 102.01, 604/43–45, 258, 276, 508, 510, 523, 284
See application file for complete search history.

(56) References Cited

U.S. PATENT DOCUMENTS

| 4,235,231 A * | 11/1980 | Schindler et al. ........... 604/6.09 |
| 4,329,994 A | 5/1982 | Cooper |
| 4,573,966 A * | 3/1986 | Weikl et al. ................... 604/509 |
| 4,636,195 A * | 1/1987 | Wolinsky ....................... 604/509 |
| 4,929,238 A * | 5/1990 | Baum ............................ 604/218 |
| 4,979,942 A | 12/1990 | Wolf et al. |
| 5,106,363 A | 4/1992 | Nobuyoshi |
| 5,135,484 A * | 8/1992 | Wright ............................ 604/28 |
| 5,222,941 A * | 6/1993 | Don Michael ............. 604/103.1 |
| 5,261,877 A * | 11/1993 | Fine et al. ..................... 604/540 |
| 5,290,259 A * | 3/1994 | Fischer ......................... 604/218 |
| 5,370,609 A * | 12/1994 | Drasler et al. .................. 604/22 |
| 5,380,284 A | 1/1995 | Don Michael |
| 5,462,529 A * | 10/1995 | Simpson et al. ......... 604/101.04 |
| 5,616,120 A * | 4/1997 | Andrew et al. ................. 604/28 |
| 5,643,206 A | 7/1997 | Fischer |

(Continued)

FOREIGN PATENT DOCUMENTS

| DE | 19757224 A1 | 7/1999 |
| WO | WO 00/03651 | 1/2000 |
| WO | WO 01/15767 | 3/2001 |

OTHER PUBLICATIONS

European Application No. 10007840.1, European Extended Search Report dated Oct. 11, 2010, European Patent Office, 7 pages.

(Continued)

*Primary Examiner* — Kevin C Sirmons
*Assistant Examiner* — Andrew Gilbert

(57) ABSTRACT

Fluid delivery systems capable of introducing first and second fluids into first and second lumens of a multi-lumen catheter are provided. The first and second fluids are generally a dissolution fluid and a dissolution fluid attenuating fluid. Also provided are fluid delivery devices and kits that include the subject systems. The subject fluid delivery systems find use in a variety of different applications, and are particularly suited for use in the chemical ablation of internal vascular lesions.

2 Claims, 5 Drawing Sheets

U.S. PATENT DOCUMENTS

| | | | |
|---|---|---|---|
| 5,735,811 A * | 4/1998 | Brisken | 604/22 |
| 5,827,219 A * | 10/1998 | Uber et al. | 604/30 |
| 5,925,016 A * | 7/1999 | Chornenky et al. | 604/96.01 |
| 6,290,689 B1 * | 9/2001 | Delaney et al. | 604/507 |
| 6,533,767 B2 * | 3/2003 | Johansson et al. | 604/507 |
| 6,540,715 B1 | 4/2003 | Kühn et al. | |
| 6,730,063 B2 * | 5/2004 | Delaney et al. | 604/173 |
| 6,827,710 B1 * | 12/2004 | Mooney et al. | 604/500 |
| 2007/0191781 A1 | 8/2007 | Richards et al. | |

OTHER PUBLICATIONS

European Application No. 01964100.0, Office Action dated Oct. 7, 2011, European Patent Office, 4 pages.

* cited by examiner

FLUID DELIVERY SYSTEMS FOR DELIVERING FLUIDS TO MULTI-LUMEN CATHETERS

INTRODUCTION

This application is a continuation application of U.S. patent application Ser. No. 09/648,282, filed on Aug. 24, 2000, now abandoned, which is incorporated by reference in its entirety herein.

1. Field of the Invention

The field of this invention is atherosclerosis and related vascular conditions, and particularly catheter devices used for treating such conditions.

2. Background of the Invention

The formation of plaques or lesions, (atherosclerotic plaques or lesions) on vascular tissue, such as the inner surface of blood vessels, aortic valves, etc., is a major component of various vascular disease conditions. For example, plaques on heart related vascular structures, e.g., coronary artery intima, heart valves, etc., are often implicated in various heart disease conditions. Likewise, plaques or lesions present on the intima of peripheral vessels, e.g., arteries, are often implicated in various peripheral vascular disease conditions.

A variety of different protocols have been developed for treating diseases associated with the presence of vascular lesions or plaques. Such treatment methodologies generally involve mechanical removal or reduction of the lesion, and include: bypass surgery, balloon angioplasty, mechanical debridement, atherectomy, valve replacement, and the like. Despite the plethora of different treatment strategies that have been developed for the treatment of such vascular disease conditions, there are disadvantages associated with each technique, such as tissue damage, invasiveness, etc. For example, restenosis is a common complication that results in arteries in which lesions have been mechanically removed.

As such, there is continued interest in the development of new treatment protocols for the removal of vascular lesions from vascular tissue, as well as catheter devices that are used in such protocols.

Relevant Literature

U.S. Patents of interest include: U.S. Pat. Nos. 6,063,052; 6,048,334; 6,042,565; 5,997,502; 5,947,935; 5,944,694; 5,916,197; 5,827,219; 5,795,333; 5,741,232; 5,520,653; 5,383,858; 4,854,324; 4,677,980; and 4,370,982. Also of interest are U.S. Pat. Nos. 4,329,994; 4,838,881; 5,149,330; 5,167,623; 5,207,648; 5,542,937; 6,004,310; and 6,013,068. Also of interest are U.S. Pat. Nos. 4,445,892; 4,573,966; 4,610,662; 4,636,195; 4,655,746; 4,824,436; 4,911,163; 4,976,733; 5,059,178; 5,090,960; 5,167,628; 5,195,955; 5,222,941; 5,380,284; 5,443,446; and 5,462,529. See also: WO 00/03651, the disclosure of which is herein incorporated by reference.

SUMMARY OF THE INVENTION

Fluid delivery systems capable of introducing first and second fluids into first and second lumens of a multi-lumen catheter at predetermined flow rates, and often substantially the same flow rates are provided. The first and second fluids are generally a dissolution fluid and a dissolution fluid attenuating fluid. Also provided are fluid delivery devices and kits that include the subject systems. The subject fluid delivery systems find use in a variety of different applications, and are particularly suited for use in the chemical ablation of internal vascular lesions.

DESCRIPTION OF THE SPECIFIC EMBODIMENTS

Figure 1:
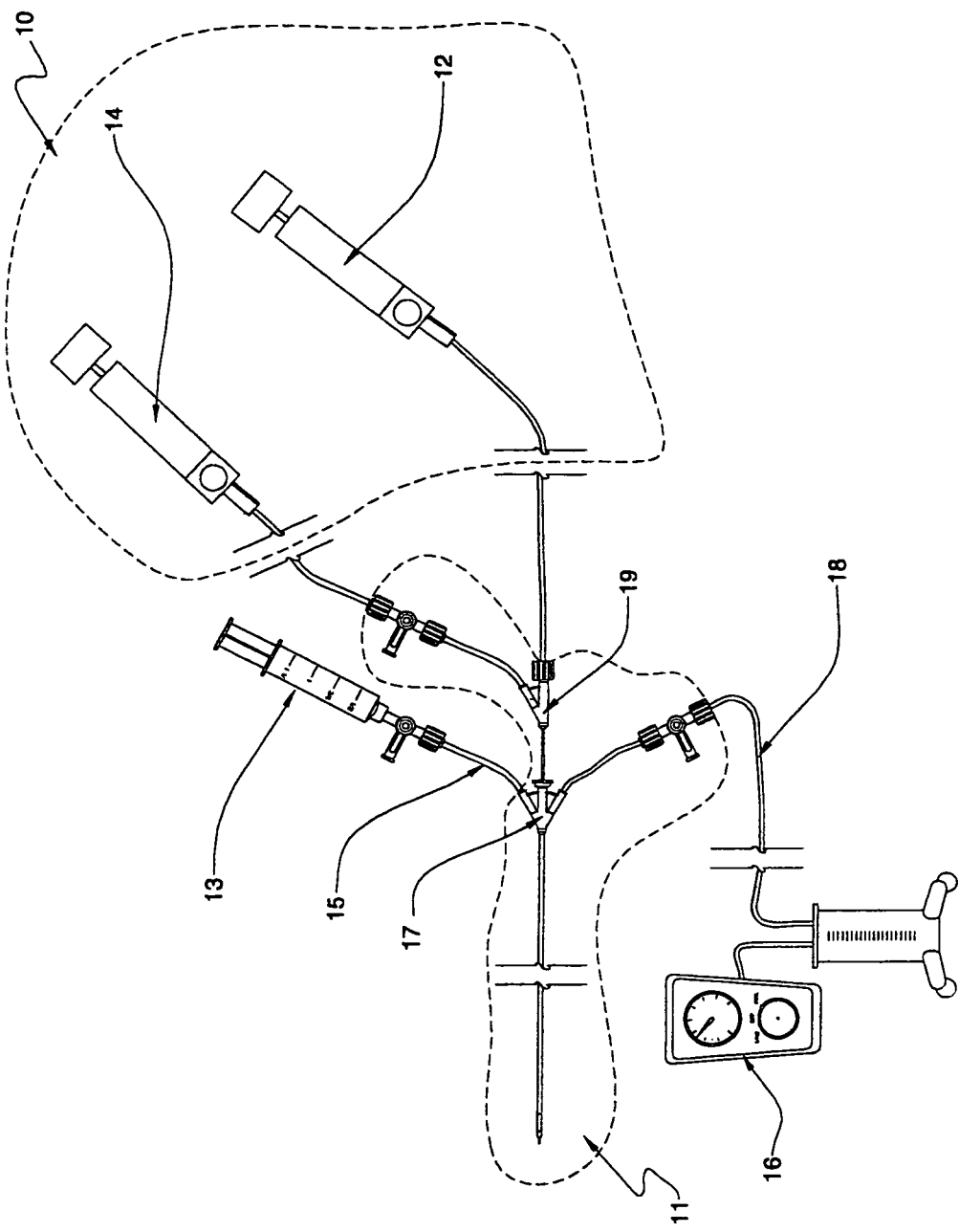
FIG. 1 provides a representation of a fluid delivery system according to a first embodiment of the subject invention.

Fluid delivery systems capable of introducing first and second fluids into first and second lumens of a multi-lumen catheter at a predetermined, and often at substantially the same, flow rate are provided. The first and second fluids are generally a dissolution fluid and a dissolution fluid attenuating fluid. Also provided are fluid delivery devices and kits that include the subject systems. The subject fluid delivery systems, devices and kits find use in a variety of different applications, and are particularly suited for use in the chemical ablation of internal vascular lesions, particularly where a vascular site is flushed with a dissolution fluid and a dissolution fluid attenuating fluid. In further describing the subject invention, the subject fluid delivery systems will be described first, both generally and in terms of the figures, followed by a description of: (a) representative methods in which the subject systems find use; and (b) and the subject kits.

Before the subject invention is described further, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims.

It must be noted that as used in this specification and the appended claims, the singular forms "a," "an," and "the" include plural reference unless the context clearly dictates otherwise. Unless defined otherwise all technical and scientific terms used herein have the same meaning as commonly understood to one of ordinary skill in the art to which this invention belongs.

Fluid Delivery Systems

As summarized above, the present invention provides systems for delivering at least two different fluids into separate lumens of a multi-lumen catheter, where the fluids are introduced into the two different lumens of the multi-lumen catheter at a predetermined or set flow rate. By predetermined or set flow rate is meant that the flow rate is known and controlled in a known manner, e.g., as is accomplished using a metered or automated fluid delivery means, such as described in U.S. Pat. No. 6,063,052, the disclosure of which is herein incorporated by reference.

In many embodiments, the first and second fluids are delivered by the subject fluid delivery systems to the first and second lumens, respectively, at substantially the same flow rate. In other words, in many embodiments the subject systems are capable of delivering a first fluid into one lumen of a multi-lumen catheter at a flow rate that is substantially the same as, if not identical to, the flow rate of a second fluid that is introduced by the system into a second lumen of the same multi-lumen catheter. By "substantially the same as" is meant that any variation in flow rates, if present at all, between the first and second introduced fluids does not exceed about 10 cc/min, and usually does not exceed about 2 cc/min in magnitude.

A feature of the subject systems is that they include a means for delivering at least two different fluids, i.e., a fluid dispensing means, into separate lumens of a multi-lumen catheter, where, in many embodiments, each of the different fluids introduced by the subject means is delivered into its respective lumen of the multi-lumen catheter at substantially the same, if not the same, flow rate. Generally, the subject fluid dispensing means is a means for moving first and second fluids out of first and second fluid reservoirs and into first and second lumens of a multi-lumen catheter, where the fluid reservoirs are generally in fluid communication with their respective lumens of the multi-lumen catheter by tubing or analogous fluid conveyance means, where the connections between the reservoir, tubing and lumens may include valves, stop-cocks etc., as desirable, where a multitude of different connection means are known to those of skill in the art.

The subject fluid dispensing means may be made up of a single, integral structure or two or more disparate and readily separable elements, but typically includes the following components: two distinct fluid reservoirs and a means for increasing the internal pressure in each distinct fluid reservoir, i.e., a pressurization means. The first and second fluid reservoirs have a volume sufficient to hold an amount of fluid that is requisite for the intended use, where the volume of each reservoir is generally at least about 50, usually at least about 100 and more usually at least about 120 ml, where the volume may be as great as about 400 ml or greater, but generally does not exceed about 150 ml and usually does not exceed about 120 ml. Each fluid reservoir is further characterized by generally having a single fluid port by which fluid leaves the reservoir upon increase of internal pressure inside the fluid reservoir. The single fluid port or opening generally includes a removable sealing means, e.g., a valve or analogous structure, that can be opened to provide for fluid flow through the port. The diameter of the port is large enough to provide for the desired fluid flow rate out of the reservoir, and typically ranges from about 1 to 5 mm, usually from about 1 to 2 mm.

As mentioned above, the subject fluid dispensing means include two different fluid reservoirs, i.e., a first and second fluid reservoir. The first fluid reservoir houses or stores a quantity of a dissolution fluid, while the second fluid reservoir houses or stores a quantity of a dissolution fluid attenuating fluid. Where the target lesion is made up of organic matter, of interest as dissolution fluids and dissolution fluid attenuating fluids are surfactant/detergent solutions and dilution solutions (e.g., saline, water), such as those described in U.S. patent application Ser. No. 09/528,576; the disclosure of which is herein incorporated by reference. In other embodiments where the target lesion comprises inorganic matter, acidic dissolution solutions and their companion pH elevating, e.g., buffer, attenuating fluids are of interest, such as those described in WO 00/03651; the disclosure of which is herein incorporated by reference.

The first and second fluid reservoirs are designed such that the internal pressure of the reservoirs can be increased to provide for fluid flow at a desired or set flow rate, i.e., a predetermined metered flow rate, out of the reservoir through the fluid port. The internal pressure of the reservoir may, in general, be increased using any convenient protocol, e.g., by introduction of a gas into the reservoir. As such, in many embodiments, the fluid reservoirs are compressible, by which is meant that one or more walls of the reservoirs may be moved relative to the others in a manner that provides for a decrease in the volume of the reservoir (and concomitant expulsion of fluid out the port), where the one or more walls of the reservoir is movable upon application of a sufficient force to the wall. Generally, the amount of force required to move the wall of the reservoir ranges from about 50 to 1000 lb, usually from about 200 to 800 lb and more usually from about 500 to 600 lb. Where the fluid reservoirs are compressible, they should be capable of going from a first volume to a second volume, where the second volume is typically less than 10%, usually less than 5% and more usually less than 1% of the first volume.

The first and second fluid reservoirs may be present in a single, integral component of the fluid delivery means or present as two disparate components, depending on the nature of the fluid delivery means. Representative configurations of the first and second fluid reservoirs relative to each other are reviewed below.

The other essential component of the fluid dispensing means is a means for increasing the internal pressure of each fluid reservoir to provide for fluid exit from the reservoir in a controlled or metered manner. This pressurization means may take a variety of different configurations, depending on the particular fluid dispensing means in which it is located. As discussed above, the fluid reservoirs in many embodiments of the subject invention are ones that are compressible. As such, in many embodiments of the invention, the pressurization means is a means for compressing one or more walls of the fluid reservoir in a manner sufficient to provide for the desired increase in pressure and the concomitant metered flow of fluid out of the reservoir through the port. In these embodiments, the means for the compressing one or more walls of the reservoir, i.e., the compression means, is typically a flat or planar element and a means for pushing the flat or planar element against one side of the reservoir with a force sufficient to compress the reservoir, where the force typically ranges from about 50 to 1000, usually from about 200 to 800 and more usually from about 500 to 600 lb, as described above.

As with the fluid reservoirs, this pressurization means may be present in a variety of different configurations depending on the particular nature of the fluid delivery means, e.g., whether it is a single integral component or made up of disparate components, which disparate components may or may not be physically together during use. As such, in certain embodiments the pressurization means is made up of two distinct and separately controllable or actuatable compression means, while in other embodiments the pressurization means is made up of a single actuatable compression means which is capable of simultaneously compressing both reservoirs.

As mentioned above, the fluid delivery means may be made up of a single, integral structure or two more disparate structures, which disparate structures may or may not be physically together during use. An example of a fluid delivery means made up of two physically distinct disparate structures is two separately actuatable metered fluid delivery devices, e.g., two separate metered fluid dispensing devices, e.g., as described in U.S. Pat. Nos. 6,063,052; 6,048,334; 6,042,565; 5,997,502; 5,947,935; 5,944,694; 5,916,197; 5,827,219; 5,795,333; 5,741,232; 5,520,653; 5,383,858; 4,854,324; 4,677,980; and 4,370,98; the disclosures of which are herein incorporated by reference, where each device has one of the two fluid reservoirs and thereby houses one of the two fluids, e.g., the dissolution fluid and the dissolution fluid attenuating fluid. In other embodiments of the fluid delivery means, the first and second fluid reservoir are present in the same structure, which structure also includes a pressurization means that is capable of compressing the first and second fluid reservoirs, as described above. The fluid reservoirs of this embodiment of the fluid delivery means may or may not be capable of being readily removed from the remainder of the structure, e.g., where the fluid reservoirs are present in a cartridge, as described in greater detail below. The pressurization means may be made up of two separately actuatable compression means or a single compression means that includes two different planar elements, e.g., an element for reach fluid reservoir.

The subject fluid delivery systems are designed for delivering a dissolution fluid and a dissolution fluid attenuating fluid into two separate lumens of a multi-lumen catheter or multi-lumen catheter system, where each fluid is delivered at a desired flow rate. Generally, the flow rate of each fluid is at least about 05 cc/sec, usually at least about 1 cc/sec and more usually at least about 2 cc/sec, where the flow rate may be as great as 5 cc/sec or greater, but generally does not exceed about 1 cc/sec and usually does not exceed about 2 cc/sec. As mentioned above, in many embodiments, the subject systems are capable of delivering the two different fluids to their respective lumens at substantially the same flow rate. In other embodiments, the subject systems are capable of delivering two different fluids at rates that are not substantially the same, but are fixed relative to each other, e.g., a fixed ratio, such that the two different fluids may be delivered at different rates that are nonetheless substantially constant and are therefore delivered at a fixed ratio of rates.

The subject fluid delivery systems may be employed with a variety of different multi-lumen catheters. Representative multi-lumen catheter devices that may be adapted for use in the subject methods include those described in U.S. Pat. Nos. 329,994; 4,838,881; 5,149,330; 5,167,623; 5,207,648; 5,542,937; and 6,013,068; the disclosures of which are herein incorporated by reference. The subject fluid delivery systems are particularly suited for use in delivering fluid to the multi-lumen catheters described in U.S. patent application Ser. Nos. 10/101,544; 09/425,826; 09/384,860; and 09/528,576; as well as PCT Publication No. WO 00/03651; the disclosures of which are herein incorporated by reference.

Representative fluid delivery systems according to the subject invention are described in greater detail in terms of the figures. FIG. 1 provides a representation of a fluid delivery system according to a first embodiment of the subject invention. In FIG. 1, fluid delivery system 10 is shown connected in fluid communication with multi-lumen catheter system 11 as would be found during use of the subject delivery system. Fluid delivery system 10 is made up of two separate metered fluid delivery means or dispensing means 12 and 14, as described above, which devices are capable of providing for a controlled, metered flow of fluid, e.g., dissolution fluid or dissolution fluid attenuating fluid housed in the reservoirs present therein. Dispensing means 12 includes first fluid reservoir filled with dissolution fluid and dispensing means 14 includes the second fluid reservoir filled with dissolution fluid attenuating fluid. Multi-lumen catheter system 11 includes aspiration catheter 17 and total occlusion catheter 19. Also shown are balloon inflation line 15, balloon inflation syringe 13, aspiration line 18 and negative pressure source 16.

Figure 2A:
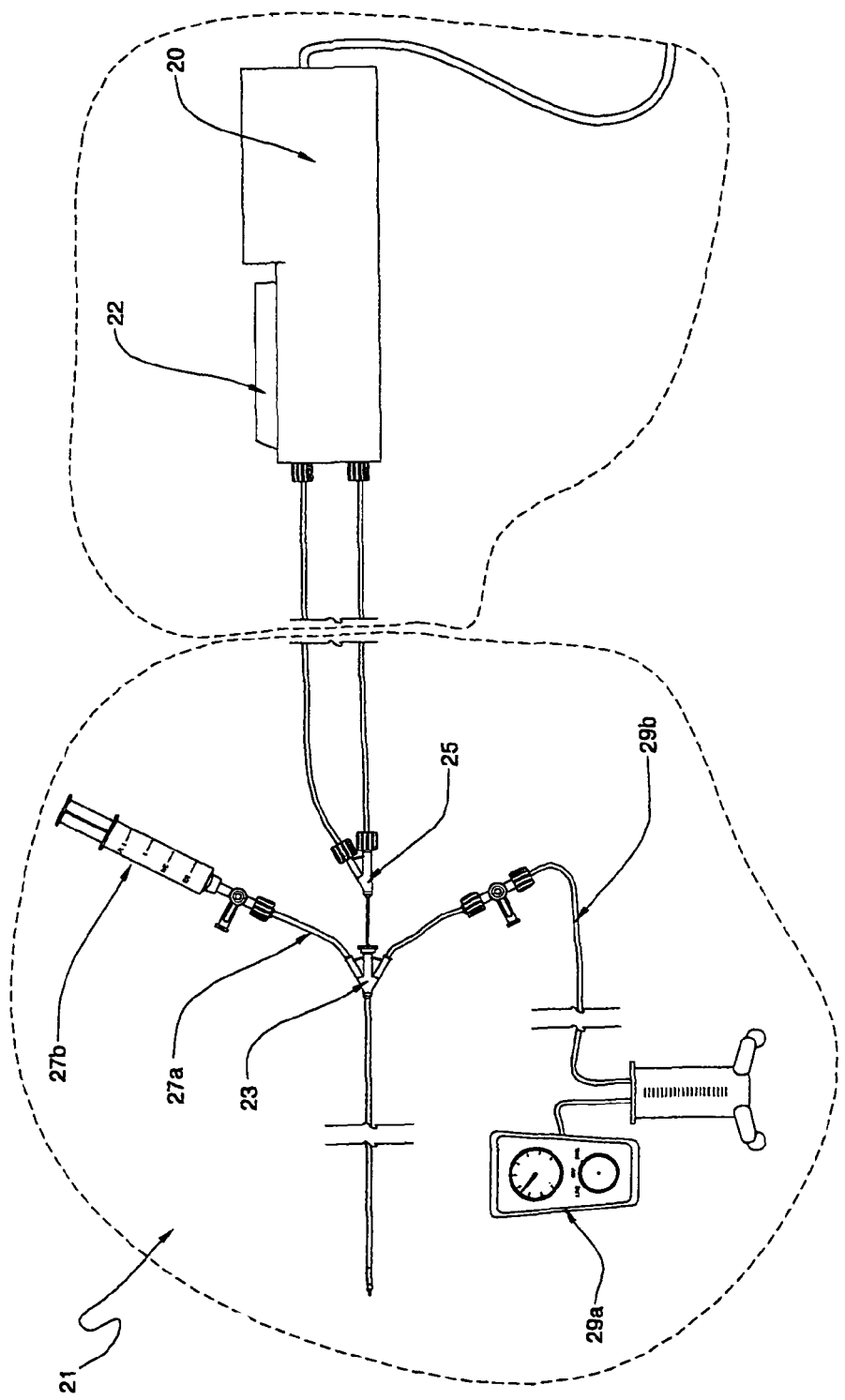
FIGS. 2A to 2C provide a representation of a second embodiment of the subject fluid delivery system.
Figure 2B:
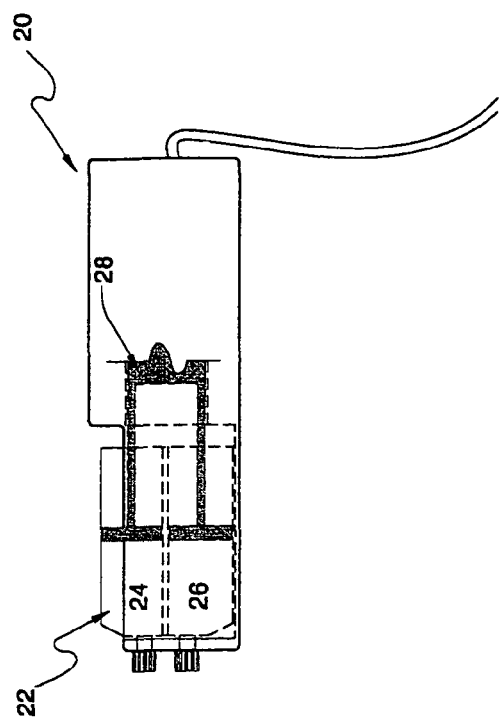
Figure 2C:
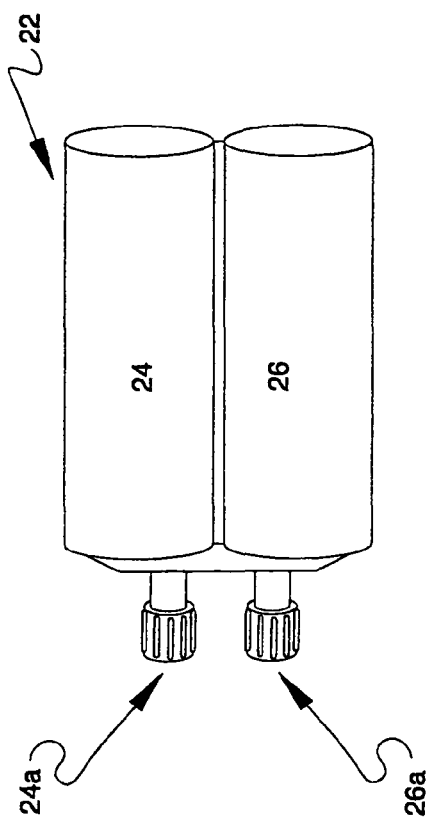

FIGS. 2A to 2C provide a representation of a second embodiment of the subject fluid delivery systems. In FIG. 2A, fluid delivery system 20 is shown operationally connected to multi-lumen catheter system 21. Fluid delivery system 20 is a single integral structure which is pneumatically or analogous powered and includes cartridge 22 that includes the first and second fluid reservoirs filled, respectively, with dissolution fluid and dissolution fluid attenuating fluid. The multi-lumen catheter system 21 includes aspiration catheter 23 and total occlusion catheter 25, where the system is shown attached to balloon inflation syringe 27b via balloon inflation line 27a and negative pressure source 29a via aspiration line 29b. FIG. 2B provides a cutaway view of the fluid dispensing means 20 shown in FIG. 2A. As shown in FIG. 2B, present in fluid dispensing means 20 are first and second fluid reservoirs 24 and 26, as well as compressing means 28. Compressing means 28 is a unified system that is capable of compressing both first and second fluid reservoirs simultaneously. FIG. 2C provides a representation of the disposable cartridge 22 that fits into the pressurization means, made up of the compressing means 28 and the actuation means thereof, e.g., the pneumatic actuation means, to produce the fluid delivery means 20. The disposable cartridge 22 includes filled fluid reservoirs 24 and 26, which fluid reservoirs each have a single opening 24a and 26a which allows fluid to flow out of the reservoirs upon compression of the reservoirs by the compression means. The fluid openings 24a and 26a are standard luer connectors.

Figure 3:
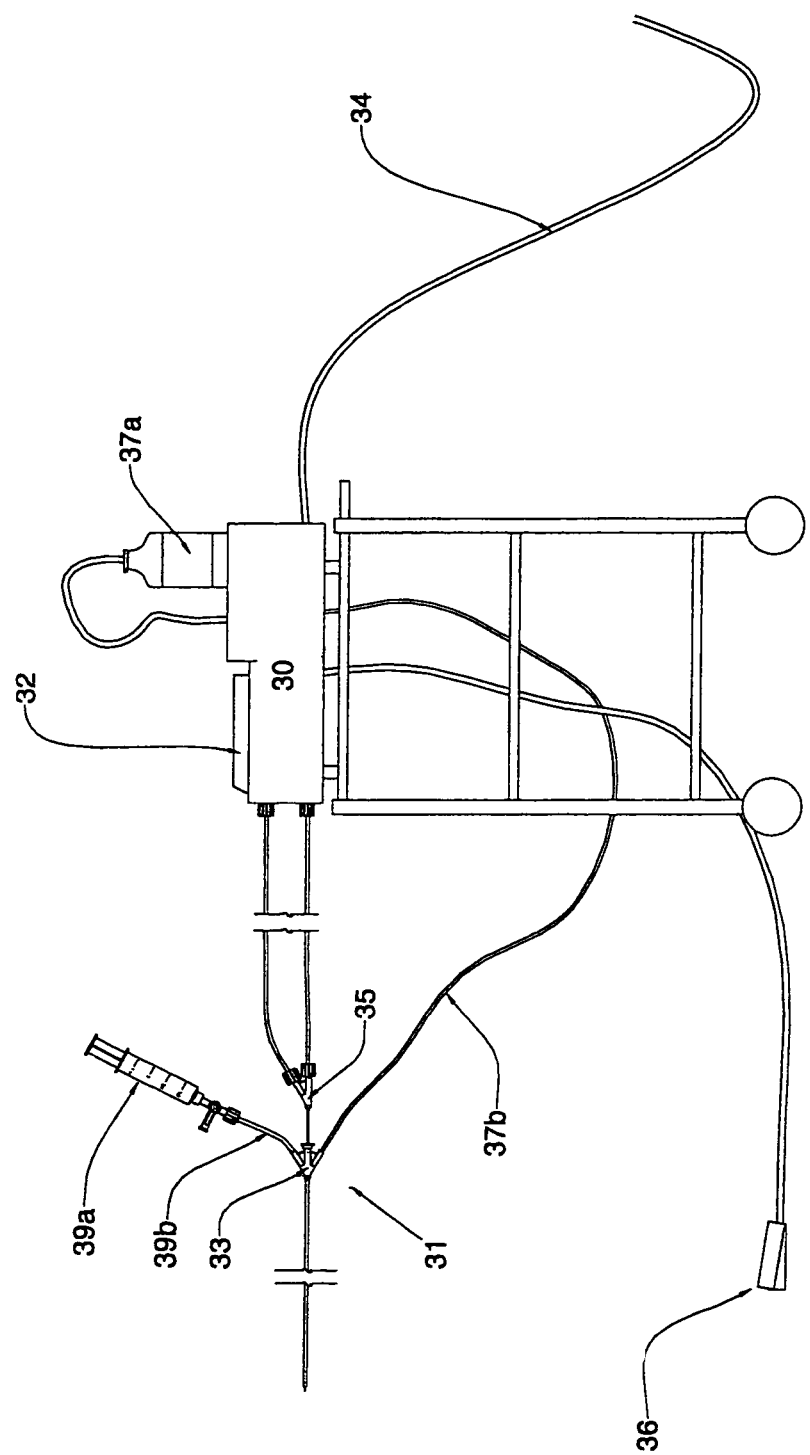
FIG. 3 provides a depiction of yet another embodiment of the subject fluid delivery system.

FIG. 3 provides a depiction of yet another embodiment of the subject fluid delivery system. In FIG. 3, fluid delivery system 30 includes disposable cartridge 32 which houses the first and second fluid reservoirs (not shown). The first and second fluid reservoirs are operationally connected with multi-lumen catheter system 31, which system is made up of aspiration catheter 33 and total occlusion catheter 35. Also shown is balloon inflation syringe 39a connected to aspiration catheter 33 via balloon inflation line 39b. The fluid delivery system is actuated by a compressed air source (not shown) to which the delivery system 30 is connected via compressed air line 34. The delivery system is controlled via foot switch 36. Also shown is disposable vacuum bottle 37a which is connected to the multi-lumen catheter system via aspiration line 37b and serves as the negative pressure source. Aspiration can be triggered via foot switch 36. Fluid delivery means 30 includes a holder for the vacuum bottle 37a.

Figure 4:
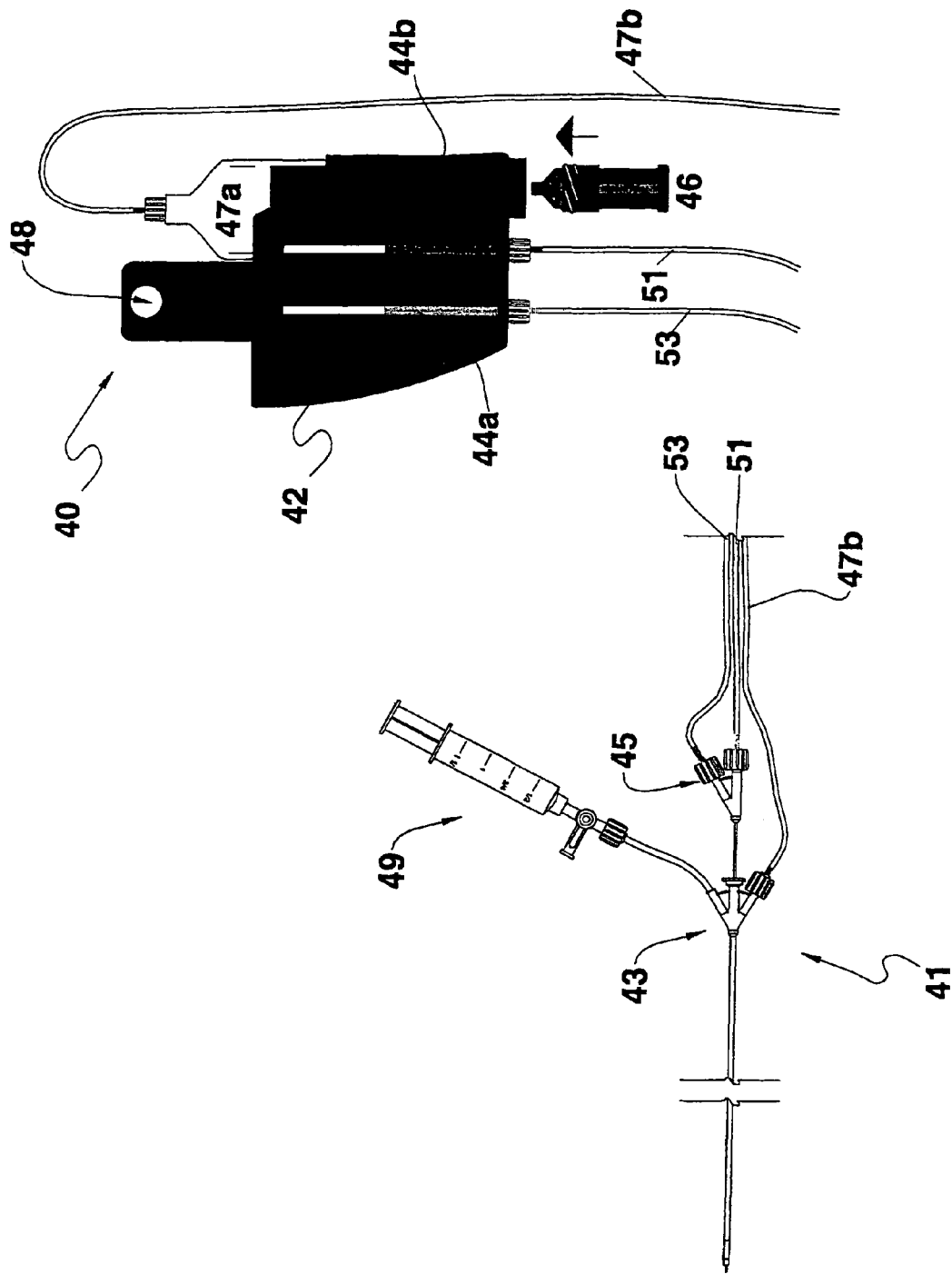
FIG. 4 provides a representation of yet another embodiment of the subject fluid delivery system.

FIG. 4 provides a representation of yet another embodiment of the subject fluid delivery system. In FIG. 4, fluid delivery system 40 is made up of a housing 42 which houses the first and second reservoirs which may be viewed through windows 44a and 44b. Housing also includes compression means, not shown, which is actuated by compressed gas cartridge 46. As such, housing 42 includes a cartridge receiving area or holder. Also present on housing 42 is a vacuum bottle holder for holding a vacuum bottle 47a which serves as the negative pressure means of the system. The fluid delivery means is designed to be hung on a hook via hole 48. Also shown in FIG. 4 is multi-lumen catheter system 41, which is made up of aspiration catheter 43 and total occlusion catheter 45. Also shown is balloon inflation syringe 49. During use, dissolution fluid tubing 51 and attenuating fluid tubing 53 establish fluid communication between the first and second reservoirs of the fluid delivery device and the total occlusion catheter of the multi-lumen catheter system. In addition, vacuum bottle 47a is connected to the aspiration catheter 43 via aspiration line 47b.

Methods

The subject fluid delivery systems find use in applications where it is desired to flush a vascular target site with two different fluids, particularly at the same time or simultaneously. As mentioned above, by flush is meant that the fluid is introduced into the vascular site and removed from the vascular site in manner such that the vascular site remains substantially isobaric, i.e., the pressure in the vascular site remains substantially constant. While the subject systems can, in principle, be employed to flush a vascular site with any two fluids, they are particularly suited for use in applications where chemical tissue ablation at a target vascular site is desired. As such, the subject systems find particular use in the treatment of vascular lesions or obstructions, where the target lesions or obstructions may be organic, inorganic or composite structures of both organic and inorganic components. In such embodiments, the systems are used to flush the target vascular site, and therefore the lesion or obstruction located therein, with a dissolution fluid and a dissolution fluid attenuating fluid.

In these embodiments of the subject methods, the first step is generally to provide for an entry site for the multi-lumen catheter into the vascular system of the host. Entry is typically provided by placement of an introducer sheath at a convenient location, e.g., leg etc., as is known in the art. A guidewire is then inserted through the entry sheath and its distal end is placed at the target vascular site. Next, the multi-lumen catheter system is positioned inside the vascular system, where the particular protocol for this positioning step generally depends on the nature of the particular multi-lumen catheter being employed.

Following positioning of the multi-lumen catheter, fluid communication is established between a first lumen of the catheter and the first fluid reservoir and a second lumen of the catheter and the second fluid reservoir. Fluid communication is typically established by connecting the first lumen to the port of the first reservoir and the second lumen to the port of the second reservoir, typically via a connecting tube or analogous fluid conveyance means.

Following establishment of fluid communication, as described above the fluid delivery means is actuated in a manner to provide for fluid flow from the first and second reservoirs into the first and second lumens, respectively, of the multi-lumen catheter. The flow rate of fluid into the first and second lumens typically ranges from about 0.5 to 5 cc/sec, usually from about 0.5 to 3.0 cc/sec and more usually from about 1 to 2 cc/sec.

In this manner the dissolution fluid and dissolution fluid attenuating fluid are introduced into the vascular site. via the appropriate lumens inside the multi-lumen catheter. In addition, fluid is removed from the vascular site via another lumen of the multi-lumen catheter, e.g., the aspiration lumen of the multi-lumen. The target vascular site is flushed with the dissolution and dissolution fluid attenuating fluids for a period of time sufficient to result in the desired amount of treatment, e.g., target lesion size reduction, enhancement or establishment of fluid flow through the target site, etc. Following the desired amount of treatment, the system is removed from the host. More specific detail regarding the methods in which the subject systems find use can be found in U.S. patent Ser. No. 09/528,576 and publication no. WO 00/03651; the disclosures of which are herein incorporated by reference.

In certain embodiments, the methods are further characterized by the application of mechanical energy to the target lesion, e.g., to disrupt or dislodge at least a portion of the target lesion and thereby promote dissolution thereof by the dissolution fluid, e.g., by increasing the surface area of the lesion that is accessible by the dissolution fluid. Mechanical means of interest include moving structures, e.g. rotating wires, guidewires, which physically contact the target occlusion and thereby apply physical mechanical energy to the target lesion. Specific means of interest include: (a) guidewires that disrupt, dislodge, agitate or otherwise mechanically disrupt the target lesion; (b) angioplasty devices, e.g., high pressure balloons that can compress plaque against the vessel wall; (c) atherectomy devices, e.g., devices with rotating burrs that break up plaque into small pieces or can cut/excise the plaque, e.g., the Scimed Rotoblator™, Guidants' Atherocath®, etc.; (d) laser ablation devices, such as those being developed by Spectranetics; and the like.

Kits

Also provided by the subject invention are kits for use in flushing a vascular site with two fluids. The subject kits at least include first and second reservoirs, as described above, suitable for use in the subject fluid delivery systems. The first and second fluid reservoirs are generally present in the form of a cartridge or cartridges, depending on whether the fluid delivery system is a single structural unit or made up of disparate structural units, e.g., two separate metered fluid dispensing devices. The cartridge or cartridges will be filled with dissolution fluid or dissolution fluid attenuating fluid.

In addition to the filled fluid reservoirs as described above, the subject kits typically further include one or more additional components of the subject fluid delivery systems and/or components that find use in flushing a vascular site with the two fluids. Additional components of the fluid delivery system that may be present include, but are not limited to: tubing or analogous fluid conveyance means for establishing fluid communication between the reservoirs and the lumens of a multi-lumen catheter; a power source for the pressurization means of the delivery system, e.g., pressurized gas source, such as $CO_2$ cartridge; a negative pressure means, e.g., a vacuum bottle; a holder for the various components of the system; and the like.

The kits of the subject invention may also include a number of different components that find use in flushing a vascular site with the fluids of the fluid delivery systems. In many embodiments, the kits will include a multi-lumen catheter or catheter system, as described above. In certain embodiments, the kits further include a guidewire. Any convenient type of guidewire may be present, where a number of different guidewires are known to those of skill in the art. Guidewires of interest include those described in U.S. Pat. Nos. 6,007,514; 5,980,471; 5,957,865; 5,938,609; 5,931,819; 5,916,178; 5,908,395; 5,902,254; 5,865,767; 5,827,201; 5,788,654; 5,772,609; 5,769,796; 5,755,695; 5,749,837; 5,682,897; 5,660,180; 5,636,642; 5,606,981; 5,599,492; 5,596,996; 5,558,093; 5,546,948; 5,520,189; 5,507,301; 5,497,782; D363,776; 5,460,187; 5,441,497; 5,437,288; 5,427,118; 5,421,349; 5,411,033; 5,409,015; 5,368,035; 5,341,818; 5,339,833; 5,313,967; 5,303,714; RE34,466; 5,265,622; 5,238,005; 5,184,621; 5,167,239; 5,147,317; 5,144,959; 5,111,829; 5,107,852; 5,095,915; 5,095,911 5,084,022; 5,069,226; 5,063,935; 4,966,163; 4,953,553; 4,875,489; 4,827,941; 4,811,743; 4,676,249; 4,534,363; 4,080,706; 4,003,369; the disclosures of which are herein incorporated by reference. Also of interest are dilators for use in creating entries into the vascular system of the host.

Additional optional components that may be present in kits of the subject invention include various fluids and solutions in addition to the dissolution fluid and dissolution fluid attenuating fluid described above. Additional fluids that may be present include: organic matter dissolution fluids, wash or rinsing fluids,.imaging agent fluid mediums that include an imaging agent, such as a non-ionic imaging agents, e.g., CONRAY™, OXILANT™, fluids containing one or more pharmacological agents, e.g., agents that promote healing, reduce inflammation, and the like; etc.

Other components that may be present in the subject kits include one or more additional components and accessories for use with the fluid delivery means present in the kit, including tubing for connecting the various catheter components with fluid reservoirs, syringes, pumping means, etc., connectors, stop-cocks, dilators, insertion sheaths, vacuum regulators, negative pressure means, luer valve adapters, etc.

In addition to above mentioned components, the subject kits typically further include instructions for using the components of the kit to flush a vascular site with two different fluids, e.g., to flush a vascular site with a dissolution fluid and a dissolution fluid attenuating fluid. The instructions for practicing the subject methods are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging) etc. In other embodiments, the instructions are present as an electronic storage data file present on a suitable computer readable storage medium, e.g. CD-ROM, diskette, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

It is evident from the above discussion that the subject fluid delivery systems provide for a reliable and controllable way to deliver fluids to a multi-lumen catheter. As such the subject invention enhances the outcome achieved in using such catheters, e.g., in the chemical ablation of internal vascular lesions. As such, the subject invention represents a significant contribution to the art.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. A system for simultaneously flushing an internal site with two different fluids, said system comprising; (a) a multi-lumen catheter system comprising first, second and third lumens; (b) an automatic metered fluid delivery system comprising a first external reservoir containing a first fluid, which is a dissolution fluid, and a second external reservoir containing a second fluid, which is a dissolution fluid attenuating fluid, wherein said metered fluid delivery system is configured to automatically control the delivery of said first and second fluids into said first and second lumens of said multi-lumen catheter system at substantially the same flow rate to maintain to pressure substantially constant at an internal site; (c) a negative pressure means sufficient to aspirate fluid from said third lumen of said multi-lumen catheter system; (d) a balloon inflation means, including a balloon inflation lumen, wherein said dissolution fluid consisting of at least one of a surfactant/detergent solution or an acidic solution and, said dissolution fluid attenuating fluid comprising an extracorporeal fluid consisting of at least one of a dilution solution or a pH elevating solution, wherein said automatic metered fluid delivery system is configured to deliver said dissolution fluid and said dissolution fluid attenuating fluid to a target lesion in a body, each of said dissolution fluid and said dissolution fluid attenuating fluid being individually controlled by pressure regulation of the external reservoirs using a force of between about 500 pounds to about 600 pounds.

2. The system according to claim 1, wherein said first and second external fluid reservoirs are present in a cartridge.

\* \* \* \* \*

UNITED STATES PATENT AND TRADEMARK OFFICE
CERTIFICATE OF CORRECTION

| | | |
|---|---|---|
| PATENT NO. | : 8,496,620 B2 | Page 1 of 1 |
| APPLICATION NO. | : 11/267944 | |
| DATED | : July 30, 2013 | |
| INVENTOR(S) | : Constantz et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 781 days.

Signed and Sealed this
Seventeenth Day of February, 2015

Michelle K. Lee
*Deputy Director of the United States Patent and Trademark Office*